United States Patent
Kaleal, III et al.

(10) Patent No.: US 9,198,622 B2
(45) Date of Patent: Dec. 1, 2015

(54) VIRTUAL AVATAR USING BIOMETRIC FEEDBACK

(71) Applicant: Bodies Done Right, LLC, Mayfield Village, OH (US)

(72) Inventors: Robert L. Kaleal, III, Mayfield Village, OH (US); Dominic G. Carbone, Jr., Mayfield Village, OH (US)

(73) Assignee: KC Holdings I, Mayfield Village, OH (US)

( * ) Notice: Subject to any disclaimer, the term of this patent is extended or adjusted under 35 U.S.C. 154(b) by 56 days.

(21) Appl. No.: 14/049,981

(22) Filed: Oct. 9, 2013

(65) Prior Publication Data

US 2014/0100464 A1 Apr. 10, 2014

Related U.S. Application Data

(60) Provisional application No. 61/711,510, filed on Oct. 9, 2012.

(51) Int. Cl.
*A61B 5/11* (2006.01)
*A61B 5/00* (2006.01)
*A61B 5/024* (2006.01)
*A61B 5/0205* (2006.01)

(52) U.S. Cl.
CPC ................ *A61B 5/744* (2013.01); *A61B 5/0205* (2013.01); *A61B 5/02405* (2013.01); *A61B 5/11* (2013.01); *A61B 5/1121* (2013.01); *A61B 5/486* (2013.01)

(58) Field of Classification Search
CPC ...... A61B 5/0002; A61B 5/0022; A61B 5/01; A61B 5/0205; A61B 5/08; A61B 5/1116; A61B 5/1118; A61B 5/743; A61B 5/744; A61B 5/7475
See application file for complete search history.

(56) References Cited

U.S. PATENT DOCUMENTS

| | | | |
|---|---|---|---|
| 8,612,363 B2 | 12/2013 | Karkanias | |
| 2009/0047644 A1 | 2/2009 | Mensah et al. | |
| 2010/0207877 A1 | 8/2010 | Woodard | |
| 2010/0240458 A1 | 9/2010 | Gaiba et al. | |
| 2011/0082010 A1 | 4/2011 | Dyer et al. | |
| 2012/0071771 A1 | 3/2012 | Behar | |
| 2012/0271143 A1* | 10/2012 | Aragones et al. | ............. 600/407 |
| 2013/0178960 A1 | 7/2013 | Sheehan et al. | |
| 2013/0252731 A1 | 9/2013 | Dugan et al. | |

OTHER PUBLICATIONS

Anthony Parisi, "EA Sports Active Review", http://www.1up.com/reviews/ea-sports-active, May 20, 2009, 3 pgs.
Office Action for U.S. Appl. No. 14/518,808, dated Apr. 7, 2015, 22 pages.

* cited by examiner

*Primary Examiner* — Rex R Holmes
(74) *Attorney, Agent, or Firm* — Amin, Turocy & Watson, LLP

(57) ABSTRACT

Systems and methods are provided for an virtual personal trainer system using biometric feedback. The system includes a patient monitoring device configured to provide at least one metric representing a user. The system also includes a processor and a non-transitory computer readable medium storing instructions executable by the processor. The instructions can include a parameter calculation component configured to determine if the metric is outside of a predefined range and provide a parameter representing a desired behavior of the user if the metric is outside the desired range. Further, an avatar rendering component provides an avatar according to the provided parameter, such that the provided avatar represents the desired behavior. A display is also provided to display the rendered avatar to the user.

14 Claims, 5 Drawing Sheets

VIRTUAL AVATAR USING BIOMETRIC FEEDBACK

The present application claims priority to U.S. Provisional Patent Application Ser. No. 61/711,510 filed Oct. 9, 2012 entitled INTERACTIVE OVERLAY FOR VIDEO APPLICATIONS, the entire contents of which being incorporated herein by reference.

RELATED APPLICATION

The present application claims priority to U.S. Provisional Patent Application Ser. No. 61/711,510 filed Oct. 9, 2012 entitled INTERACTIVE OVERLAY FOR VIDEO APPLICATIONS, the entire contents of which being incorporated herein by reference in its entirety for all purposes.

TECHNICAL FIELD

The present invention relates generally to virtual avatar systems, and specifically to virtual avatar systems using biometric feedback.

BACKGROUND

The use of personal biometric monitoring equipment has increased the ability of individuals to more easily and more accurately collect, track and analyze data relating to the body's response to various triggers. For example, wearable sensors can monitor heart rate during an exercise program and collect and record the heart rate data for further analysis. This symbiosis of biometric monitoring and data analysis enables individuals, as well as health and fitness professionals, to better understand physiological metrics and modify the exercise or therapy program in response to the body's reaction to stressors.

Moreover, the use of virtual personalities, such as avatars, can be used to provide a graphical representation of a person or identity. One use for avatars is to provide a computer generated character through which information can be conveyed to a viewer. An avatar may have interactive capabilities, where the behavior of the avatar can be controlled or modified in response to user input.

SUMMARY

Thus, a system and method is provided herein for a virtual avatar system using biometric feedback. The system includes a patient monitoring device configured to provide at least one metric representing a user. The system also includes a processor and a non-transitory computer readable medium storing instructions executable by the processor. The instructions can include a parameter calculation component configured to determine if the metric is outside of a predefined range and provide a parameter representing a desired behavior of the user if the metric is outside the desired range. Further, an avatar rendering component provides an avatar according to the provided parameter, such that the provided avatar represents the desired behavior. A display is also provided to display the rendered avatar to the user.

Another embodiment of the present invention includes a method for providing an avatar. Included are the actions of monitoring a user performing an exercise to provide a metric representing an activity of the user; determining a parameter, representing a desired modification to the activity of the user, according the metric and patient data; and displaying an avatar to the user according to the determined parameter, such that a motion of the avatar models the desired modification to the activity of the user.

DETAILED DESCRIPTION

The Virtual Personal Trainer, or Virtual Physical Therapist, is a software application using an avatar as a user's virtual trainer to lead the user through a workout program in a manner similar to a live personal trainer.

The present invention provides a software application using an avatar whose behavior changes based on input from a user relating to physiological parameters. An avatar is a virtual representation of a personality provided to convey information to a viewer. The avatar, as described herein, is capable of changing behavior automatically in response to monitored data, representing a metric of a user's physiology, falling outside a predefined range. In order to encourage and correct the technique and behavior of the user, the avatar will react in a way designed to reflect model techniques and behavior. As one example, if the user on a treadmill is slowing down, the avatar changes behavior to demonstrate a faster pace, thereby encouraging the user to speed up. Thus, changes in the behavior of the avatar can include, but are not limited to, tone of voice, level of sound/loudness, facial expressions, body language, color, speed of movement, and range of motion. Such changes are initiated based on input from the user, including, for example, physiological changes such as heart rate, body temperature, respiration, perspiration, blood pressure, calories burned, body fat, weight, or movement that can be collected by external devices such as a heart rate monitor, pressure pads, pressure cuff, and weight scales, to name a few. In one implementation, motion capture devices, such as infrared or visible light cameras, accelerometers, and similar devices, are used to document whether the user is exercising with proper form.

In one example, for fitness applications such as physical therapy and personal training, the avatar plays the role of a virtual physical therapist or personal trainer. Based on the user's health risk assessment profile and goals, specific exercises will be recommend to either include or avoid in a workout. The user or supervisor can choose either a standard workout program or build a customized workout program by selecting one or more exercises. During the workout, the user's physiological input will automatically control the verbal commands of the avatar, as well as the avatar's movement with additional audio or text commands programmed by the trainer or medical professional. Other potential applications are any physical activities may require an instructor, coach, teacher, therapist, or avatar. Some examples are ergonometrics, dancing, yoga, zumba, and martial arts.

Figure 1:
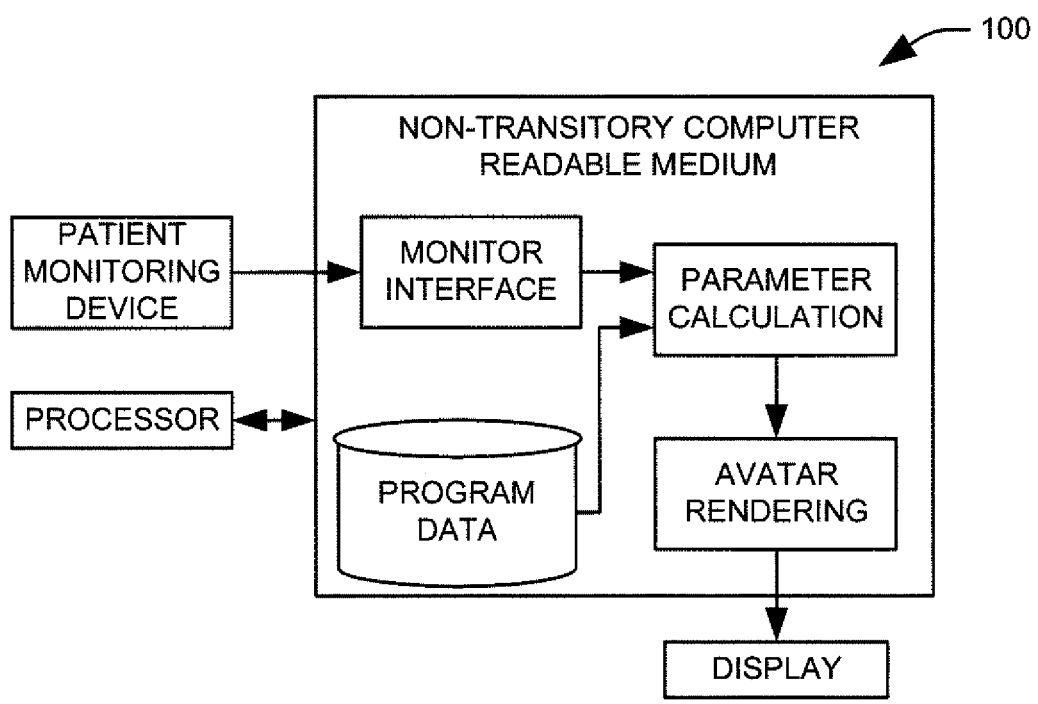
FIG. 1 illustrates an example of an virtual personal trainer system in accordance with an aspect of the invention.

FIG. 1 illustrates an example of a Virtual Personal Trainer (VPT) system 100 in accordance with an aspect of the invention. The system 100 includes a non-transitory computer readable medium 110 operatively connected to one or more patient monitoring devices 110, a processor 180, such as a computer, and a display 170, such as a monitor or television. The medium 110 further contains components for executing instructions in accordance with the system 100. A monitor interface 130 is configured to receive data from the one or more patient monitoring devices 110, whereas a program data component 150 contains information relating to a workout regime and patient and health data. Information from both the monitor interface 130 and the program data component 150 are connected to a parameter calculation component 140, where data corresponding to the monitored activity is gauged against metrics and/or goals as set by a supervisor, as well as health data. The parameter calculation component 140 then determines if the monitored activity data falls outside a predetermined range for the particular user and activity. Based on the determination, the avatar rendering component 160 modifies the avatar output in order to encourage desired behavior from the user. The avatar output is then provided to display 170 for the user.

Due to the use of technological monitoring components, sensors employed by the user can automatically and simultaneously collect and record biometric data associated with the particular workout. In one implementation, if the parameter calculation component 140 determines that the collected activity data is within the predetermined range, the avatar may provide verbal encouragement. Additionally or alternatively, if the activity data is within the predetermined range, but well below the allowed maximum, the avatar may encourage more intense activity from the user.

In another implementation, if the parameter calculation component 140 determines that the collected activity data is below a predetermined range, the avatar may respond in a manner intended to encourage a modification of the activity of the user to increase the metric that has fallen below the predetermined range. For example, the patient monitoring device 110 may be a heart rate monitor. In this example, if the program data component 150 instructs the parameter calculation component 140 that the predetermined limit is 100 beats per minute, yet the monitor interface 130 is registering 85 beats per minute from the heart rate monitor, the parameter calculation component 140 will instruct the avatar rendering component 160 to modify the avatar output. Thus, in order to increase the user's heart rate, the avatar's behavior will reflect the desired result. In this example, the avatar may visually increase the pace of the motion, provide verbal instruction to increase speed, or a visual or audible indicator can increase rhythm to encourage the user to match the pace.

Figure 2:
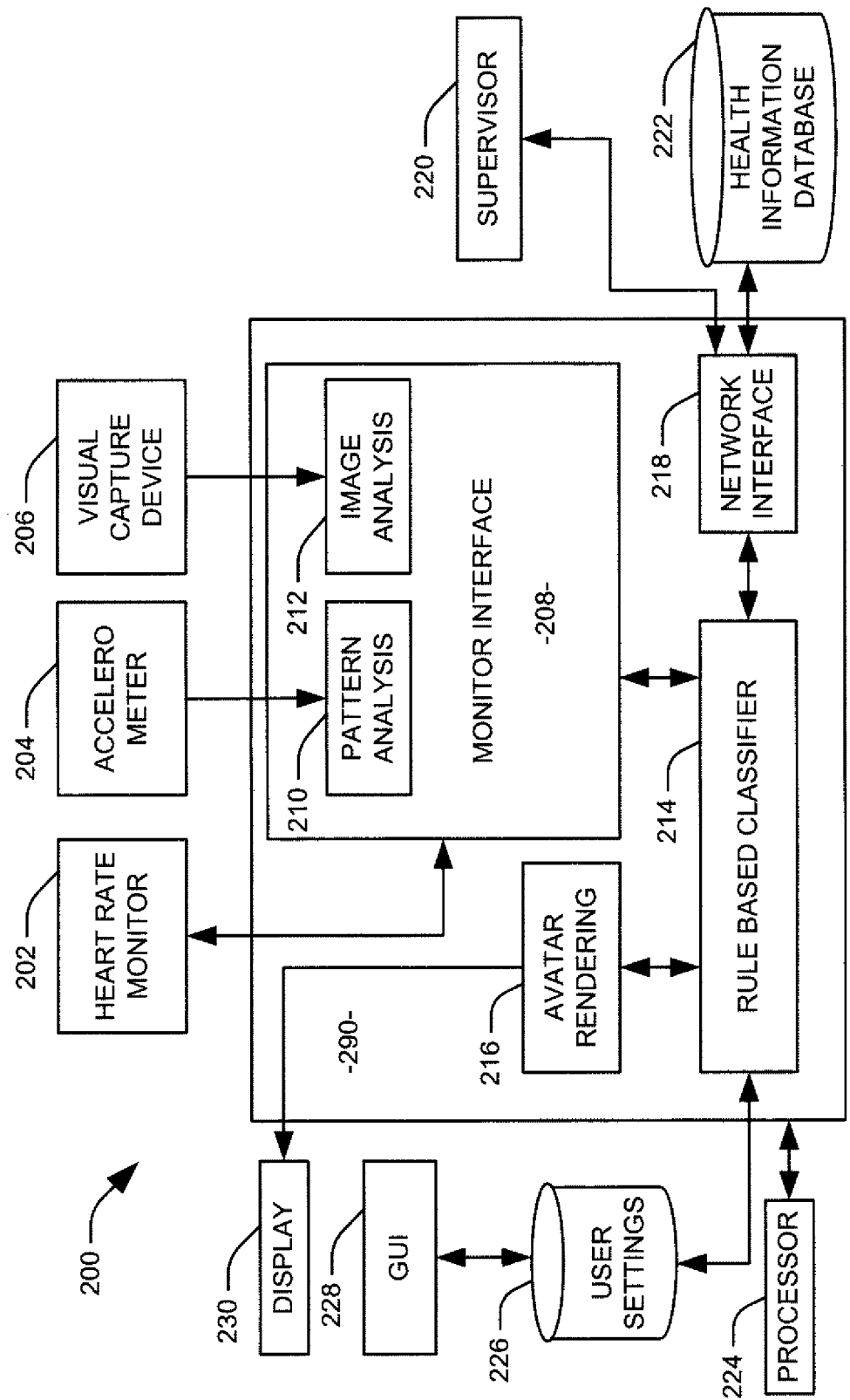
FIG. 2 illustrates another example of an virtual personal trainer system in accordance with an aspect of the invention.

FIG. 2 illustrates another embodiment of the present invention. In this example, system 200 is implemented on a computing platform 290 capable of executing computer readable instruction, as described herein. Thus, computing platform 290 contains, but is not limited to, a network interface 218, a rule based classifier 214, an avatar rendering component 216, and a monitor interface 208. The network interface 218 communicates with a supervisor 220 through a suitable device, such as a computer. The supervisor 220 can thereby provide instruction and information to the computing platform 290 regarding a particular user and exercise program. Further, a health information database 222 can provide data relating to general best practices and guidance, as well as the particular user's personal health and medical history. The personal health data provides information and guidance to the rules based classifier 214 in order to customize a workout regimen that takes the individual limitations and experience into account in formulating goals.

The monitor interface 208 is embedded with tools and programs to allow multiple monitoring devices to communicate with the computing platform 290. Although no special hardware is required, certain platforms may support certain types of sensors. For example, heart rate monitors such as heart rate monitor 202 have become a common tool for consumers, thus a variety of heart rate monitors are available to communicate with different devices, including mobile and wearable devices. Additionally, many devices incorporate an accelerometer similar to accelerometer 204, aiding in the collection of movement data. Thus, the monitor interface 208 can include tools including a pattern analysis component 210 connected to an accelerometer 204 to collect movement data from the user.

In another example, video capture technology can be employed to collect video and images of the user during a workout session. A visual capture device 206, such as a camera or other suitable device, can collect image data. The image analysis component 212 is configured to provide pattern recognition for collected movements to aid in determining if the user is properly executing the required exercises. Other examples of monitoring equipment can be biometric sensors, such as an electrocardiogram (EKG), blood oxygen level sensor, pressure pads (for balancing exercises), wireless scales (for weight and body fat), and blood pressure cuff, among others. However, the monitor interface 208 can also collect data from multiple devices that may not require additional analysis, such as heart rate monitor 202.

Once collected, the monitor interface 208 provides data to a rule based classifier 214 for further analysis. The rule based classifier 214 is configured to provide a user and a supervisor a variety of tools to customize the user experience. For example, a supervisor can customize each workout by selecting an appropriate range of motion, speed of each motion, number of repetitions, and type and intensity of exercises. Further, each user can be assigned an account, where data collected for each workout session can be stored and analyzed, as well as combined with other health data to provide a more complete picture of the individual user's health and progress. In this example, the user is provided with a graphical user interface (GUI) 228. The GUI 228 may include, for example, a remote control, a game console controller, a computer keyboard, a mouse, a smartphone, a microphone, a sensor configured to detect visible, infrared, and ultraviolet light radiating or reflected from the user, a speaker, a tablet computer, or other suitable device. Accordingly, input can be provided by the user via virtual buttons, typing a response, touching or clicking on an object on one of a display 230 or a screen of the GUI 228, verbalizing the desired response, or making a gesture representing the desired response. To this end, the GUI 228 can include appropriate pattern recognition software for recognizing responses in detected speech or gestures. The instructions from the user are filtered through user settings 226. The user settings 226 are specific to the user, according to the account set by the supervisor 220.

The input from the user is also provided to the rule based classifier 214, which is operatively connected to a processor 224, such as a computer. After the rule based classifier 214 has collected and analyzed the data provided from the monitor interface 208, network interface 218, and the user, the information is sent to an avatar rendering component 216. The avatar rendering component 216 is configured to adjust the avatar behavior according to a determination of the user's compliance with a particular workout program based on the analysis of the rule based classifier 214. For example, the avatar rendering component 216 is programmed to provide to a display 230 an avatar demonstrating the desired behavior (e.g., technique, pace) in accordance with the workout program parameters as set by the supervisor and/or the user.

Due to the automated nature of the system, as well as the fact that data is collected and analyzed in real time, the supervisor 220 can make modifications to the user's program at any time, including during an exercise session, even remotely. Patients with cardiovascular or physical limitations would benefit from having their heart rates monitored during physical activities/workouts. Although in this example, and in other examples described herein, the use of heart rate monitor 202 may be used to describe the operation of the VPT system, the system 200 can respond to collected metrics from a variety of sensors. Moreover, multiple monitoring devices can be used simultaneously, with each providing information to the system 200 for analysis. For example, in addition to wearing a heart rate monitor 202, the user can wear clothing with patches of fabric located at joints and other points of interest that reflect in the infrared spectrum. The visual capture device 206 can use those specific points to accurately determine the user's technique. Therefore, if analysis of the input from each of the monitors renders a determination that both metrics require modification, the avatar can model both a quicker pace as well as proper movement to correct both parameters simultaneously.

To continue with the example, the avatar's verbal commands and motions are automatically linked to a patient's heart rate monitor 202 via a wireless connection. Based on the patient's heart rate, the system 200 will generate an avatar through the avatar rendering component 216 to instruct the user to stay in the "zone" (optimal heart rate; e.g., speed up, or slow down), while the avatar automatically adjusting the speed/intensity of the workout, including one or both of the verbal commands from the avatar and the movement by the avatar. For one particular example, when performing alternating lateral lunges (mimicking the motion of speed skating as they are also known) when moving side to side, one's heart rate should increase. If the target heart rate is not met, the speed at which the avatar is lunging side to side will increase until the targeted heat rate is met. Conversely, if the user's heart rate exceeds the target zone, the avatar will slow down until the user's heart rate also drops. Thus, heart rate monitor 202 can be employed by the user to wirelessly upload data used by the system 200 to determine a response for display 230, as the avatar uses verbal instruction, sound and movement in real-time to coach the user through a selected exercise at a pace that is within the user's optimal range.

The system 200 can be used as a web-based application or downloaded onto a computing platform. Data can be stored locally or on a secured server to enable physical therapists, surgeons, or patients to review previous fitness sessions and progress. The VPT software can be implemented on a variety of platforms, to facilitate compliance with a particular set of goals. For example, computers, tablets, smart phones and other computing platforms are capable of communicating with heart rate monitors and other types of sensors. Therefore, by running the VPT software on a computing platform, be it a fixed setting or one that accommodates portable computing, a user can employ the VPT system to collect, analyze and respond to biometric data.

This feature is especially important for patients instructed to perform physical therapy between appointments or after they are done seeing a physical therapist. A good amount of time is needed for a physical therapists to demonstrate each required exercise, and often the patient is charged to repeat the exercise at home based solely on memory. For offsite workouts, the VPT system plays the role of the physical therapist and replaces verbal and written instructions that are forgotten or misunderstood. Again, by employing multiple patient monitors and real-time feedback, the therapists can text/email the user corrections to form, or can use live text or video chat. Alternatively, during a personal session, the VPT system will do the demonstrating so time is not wasted repeating demonstrations, and the physical therapist can focus on the patient.

For patients with potentially long recovery schedules, the appropriate exercises, number of repetitions and the range and speed of each motion can be selected for rehabilitation of a soft-tissue injury or for post-surgery for continuing offsite therapy. The VPT system will record the time, date, and physiological input to confirm that a workout was completed and at what level of intensity. The results can be analyzed to determine compliance to provide information which can be sent to the personal trainer or therapist to make needed modifications to the patient's program. The user is then notified either by text or email that changes have been made, or that the user has not logged in for some time and a status update is requested. In one example, the user can be notified in near-real time that the proper form is not being maintained. For example, the system can include an expert system (e.g., a rule-based classifier, artificial neural network, statistical classifier, etc.) to recognize a number of common errors in form for a given exercise from the motion capture data.

The automated nature of the VPT system provides a number of benefits to users as well as supervisors. For example, personal trainers typically demonstrate exercises and then have the user repeat the exercise. However, repetition is often required to ensure the user performs the exercise properly. This can be monotonous and time consuming for both the user and the supervisor. By employing the VPT system, a user can view the demonstrated exercise as needed. Further, the VPT system is configured to allow the user to alter the view, angle, and speed of the demonstrated exercise. Moreover, as the VPT system collects, analyses and responds to user input, the system can immediately provide instruction to correct performance. Using the VPT system during a personal workout session, the work of demonstrating proper technique is automatically done for each exercise which allows the trainer to focus on the user or even have the ability to work with more than one user at the same time.

Figure 3:
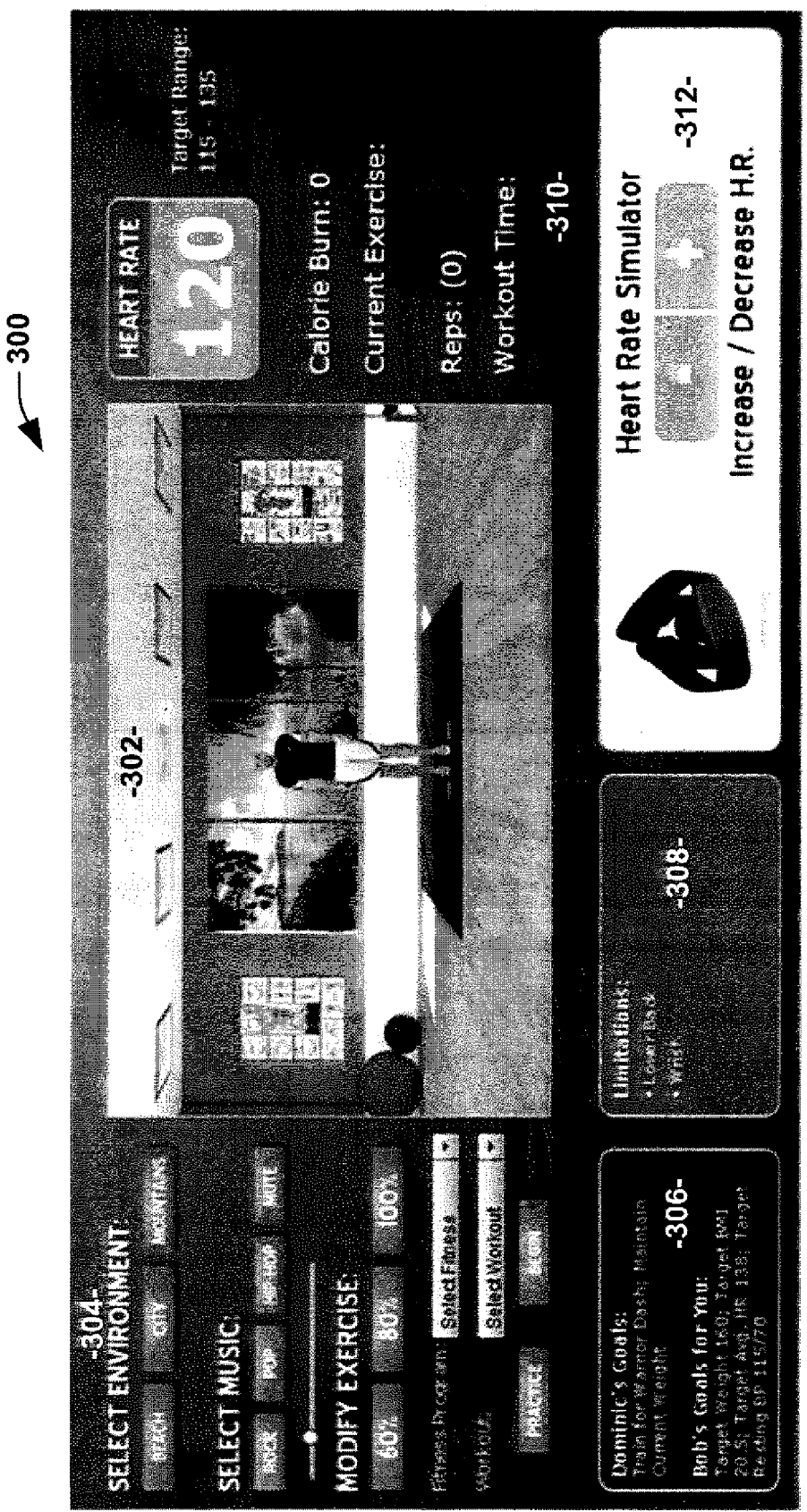
FIG. 3 illustrates an example screen shot of the virtual personal trainer system in accordance with an aspect of the invention.

FIG. 3 illustrates one example screen shot, providing a view of the display output for a user. Display 300 is a view as seen by a user during a particular workout session. In the avatar visualization space 302, the avatar is presented as a figure in a virtual environment. Control panel 304 provides a graphical interface with which the user can customize the visualization space 302. For instance, as shown, the user can select a background from beach, city or mountain setting. Further, the type of music can be adjusted. Additionally, the intensity of the workout, as well as the program and selected workout, can be adjusted.

Moreover, the avatar itself can be customized. The avatar can be constructed using an avatar component that allows an authorized party to manipulate variables to create an avatar that reflects the needs and tastes of the user. For example, the age, gender, language or accent, dress, or other visual and/or audio characteristic of the avatar may be selected to motivate and/or comfort the user. The avatar can further be customized by choosing familiar characters, such as a cartoon avatar to lead a child patient through an exercise regime, or a popular athlete during a fitness program.

Goal display 306 provides the user's proposed goals, whereas limitation display 308 reminds a viewer of possible hazards associated with the specific user or exercise program. The monitor display 312 provides information relating to the monitor or monitors being used during session. Further, monitor display 312 can provide recommendations, warnings, or additional information regarding used or available monitors. Performance compliance panel 310 displays metrics collected as well as data analyzed by the VPT system. In this example, the user's heart rate is displayed, along with the target (optimal) range. Further, the performance compliance panel 310 is configured to provide results, such as calories burned, repetitions completed, workout time, as well as the name of the current exercise and program.

By customizing and automatically responding to changes in the user's biometric data, the VPT system improves safety to the user, as users with cardiovascular or physical limitations (e.g., obese, stents) are able to monitor their heart rates during strenuous activities and analyze recorded data to avoid overworking or re-injuring a muscle group during recovery. The VPT system's verbal commands and audible and visual cues are automatically linked to the biometric monitoring tools (e.g., a heart rate monitor) via a wireless connection. In order to keep the user's heart rate in an optimal range as determined by a supervisor, a health risk assessment profile, or the user, the VPT provides instruction to the user to modify their actions to ensure their collected metrics are maintained in the optimal range. Thus, the VPT system can demonstrate to the user whether to speed up or slow down, or adjust technique as the specific exercise may require. Furthermore, users with mobility issues (e.g., limited range of motion due to surgery or injury) may have to restrict their pace, scope and repetition of their actions during recovery. In this respect, the VPT system employs user or supervisory input, as well as recorded health data, to identify particular exercises as recommended or something to avoid.

The VPT system is also configured to respond to user input automatically and in real time, thereby providing indication of a potentially dangerous activity in advance of an unsafe result. For instance, if the system recognizes certain metrics as leading to bodily harm, the system can instruct the avatar to stop the workout session and contact the supervisor or other health professional. If necessary, the VPT system can additionally or alternatively be configured to contact emergency services, thus saving precious time in the event of a severe or potentiality life threatening injury.

In another embodiment of the VPT system, the visualization space 302 can accommodate the virtual trainer avatar as well as a second avatar or other visualization. For example, if the user makes repeated actions that require demonstration, the system can collect images of the user. Thus, a side by side comparison of the user's own actions and the virtual personal trainer model technique can be displayed. The rendering of the user's technique can be by video, or image analysis can be performed to present the user as another avatar.

Figure 4:
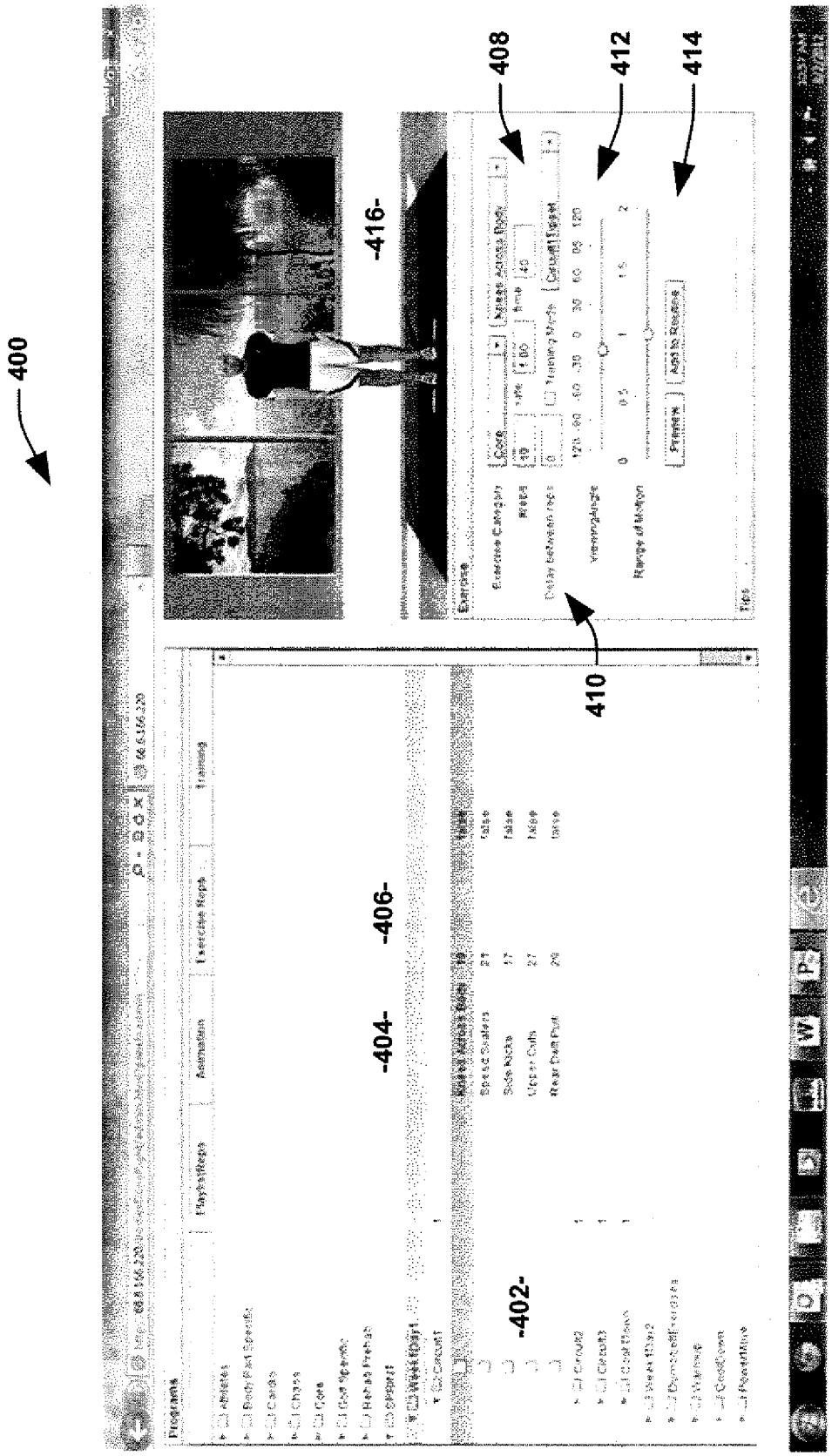
FIG. 4 illustrates another example screen shot of the virtual avatar system in accordance with an aspect of the invention.

FIG. 4 illustrates another example screen shot, providing tools to customize the VPT system. The VPT/avatar software application is designed to allow a supervisor (e.g., medical professional, physical therapist, fitness instructor) to manipulate all of the critical variables to create a workout program specifically designed to match a user's needs, physical limitations, and goals. The displayed screen 400 provides a workout and exercise customization tool. Depending on the particular application, a supervisor may maintain privileges to alter the workout regime (e.g., a group physical therapy session). As described with respect to FIG. 2, a supervisor has authority to define a set of rules to govern one or more workout sessions. Thus, the supervisor provides content for and rules to define the user experience, for example, through a server hosting software for customizing the VPT session content.

In some embodiments, a user may be authorized to customize a workout (e.g., a personalized home fitness program). Column 402 provides the capability to choose a type of workout desired, as well as to create a schedule for the workout program. Column 404 provides detailed choices to further customize the type and scope of workouts in the program. Column 406 allows for adjustment of the repetitions for each exercise selected. At 408, the speed of the repetitions can be set. Area 410 allows for an increase or decrease of the time delay between each repetition. At 412, the viewer can adjust the angle at which the avatar is displayed. For example, depending on the demonstrated exercise, a side or front view may provide a more helpful perspective of the avatar model. Additionally, the avatars range of motion can be modified at 414. This tool can be helpful when a viewer is incapable of full range of motion, thus a demonstration with a limited range of motion will more accurately reflect the desired technique. Moreover, as described with respect to FIG. 3, the avatar image and personality itself can be customized at 416.

The VPT system may also provide interactive capabilities to allow communication between supervisors and users. The system may present a question as a text status displayed on a screen, through audio (e.g., a recording by an supervisor or other content provider or machine rendered speech), or other available method. The user may then respond by use of any of multiple devices including, but not limited to, an input/output device, a microphone configured to receive an audio response, and a camera configured for gesture recognition.

A supervisor has privileged access to the program engine that includes several features that aid the supervisor in configuring an exercise sequence that guides the user experience. The supervisor gains access to the system, for example, by logging onto a server hosting the software that provides the overlay content. The supervisor may then create an account for a user, or select an existing account that the supervisor is privileged to access. Alternatively, the system assigns each user a unique account. This account can be used to tailor many of the features available from the system. For example, the account identifies the user for whom a supervisor can create rules for governing the particular user's session. The supervisor can further tailor workout sessions and provide instruction or messages for the particular user. For example, if the supervisor is a physical therapist, the supervisor may set a training goal for the user. There may be multiple customizable features available to the user to reach this goal.

Figure 5:
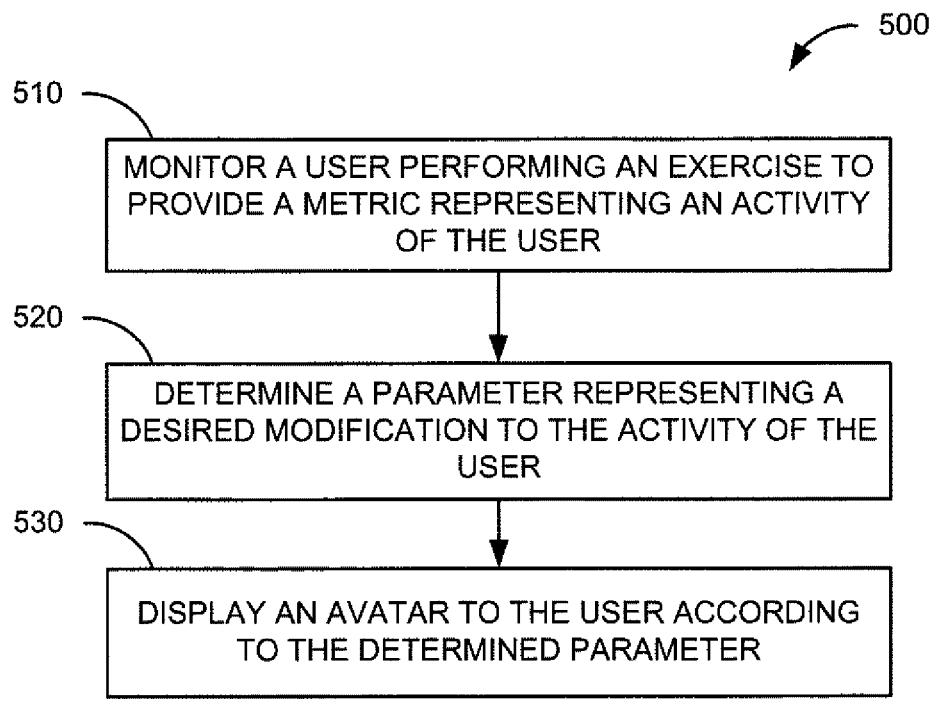
FIG. 5 illustrates an example method for providing a virtual personal trainer system in accordance with an aspect of the invention.

FIG. 5 illustrates an example of a method of operating the VPT system as laid out in a sequence 500 in accordance with an aspect of the invention. The VPT system sequence 500 can be implemented in the VPT system 100 of FIG. 1 and system 200 of FIG. 2. As such, reference is to be made to the example of FIG. 1 and FIG. 2 in the following discussion of the example of FIG. 5.

Thus, in the example of FIG. 3, a VPT system sequence 500 is outlined. The sequence begins at 310 where a user performing an exercise is monitored to provide a metric representing an activity of the user. At step 320, a parameter representing a desired modification to the activity of the user is determined according to the metric and patient data provided in step 310. At step 320, an avatar is displayed to the user in accordance to the determined parameter, such that a motion of the avatar models the desired modification to the activity of the user.

It is to be understood, however, that the interactive VPT sequence 500 is not limited to the example of FIG. 5, but that any suitable sequence may be implemented in accordance with varying rules and content as chosen by the supervisor. Further, the sequence illustrated in FIG. 5 follows only one series of method steps in a particular order, whereas the sequence may be modified by the supervisor according to the particular goal to be achieved.

Figure 6:
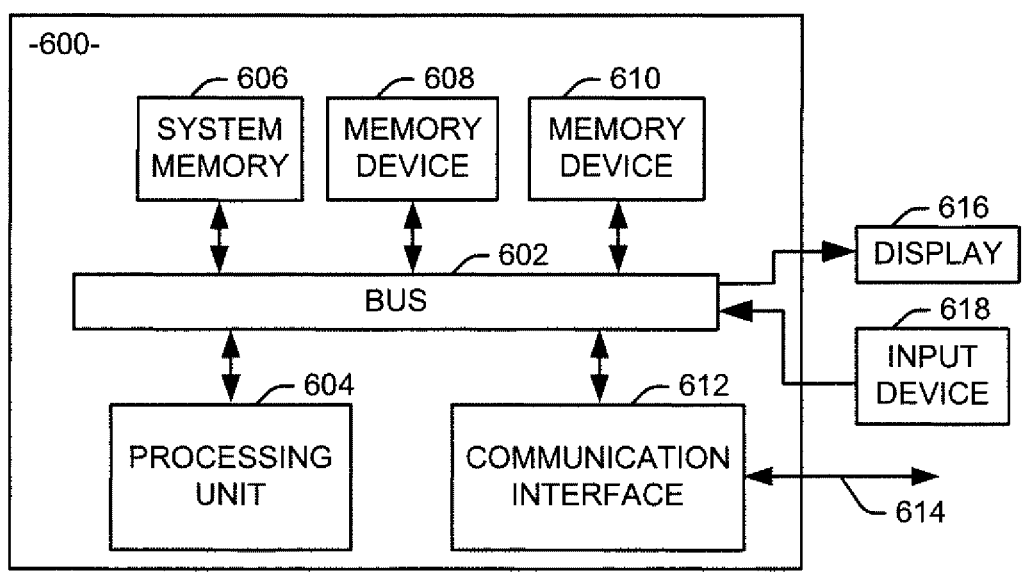
FIG. 6 is a schematic block diagram illustrating an exemplary system of hardware components capable of implementing examples of the systems and methods disclosed in FIGS. 1-5, such as the virtual personal trainer system illustrated in FIG. 1

FIG. 6 is a schematic block diagram illustrating an exemplary system 600 of hardware components capable of implementing examples of the present invention disclosed in FIGS. 1-4, such as the interactive overlay system illustrated in FIG. 1. The system 600 can include various systems and subsystems. The system 600 can be, for example, a personal computer, a laptop computer, a tablet computer, a smart portable device, a workstation, a computer system, an appliance, an application-specific integrated circuit (ASIC), a server, a server blade center, a server farm, or a similar device.

The system 600 can include a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard and/or a mouse). The system bus 602 can be in communication with the processing unit 604 and the system memory 606. The additional memory devices 608 and 610, such as a hard disk drive, server, stand alone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port. The processing unit 604 can be a computing device and can include an application-specific integrated circuit (ASIC). The processing unit 604 executes a set of instructions to implement the operations of examples disclosed herein. The processing unit 604 can include a processing core.

The additional memory devices 606, 608 and 610 can store data, programs, instructions, database queries in text or compiled form, and any other information that can be needed to operate a computer. The memories 606, 608 and 610 can be implemented as non-transitory computer-readable media (integrated or removable) such as a memory card, disk drive, compact disk (CD), or server accessible over a network. In certain examples, the memories 606, 608 and 610 can store text, images, video, and/or audio, along with appropriate instructions to make the stored data available at an associated display 616 in a human comprehensible form. Additionally, the memory devices 608 and 610 can serve as databases or data storage for the VPT system illustrated in FIG. 1. Additionally or alternatively, the system 600 can access an external data source through the communication interface 612, which can communicate with the system bus 602 and the communication link 614.

In operation, the system 600 can be used to implement a control system for an interactive overlay system that governs the interaction between the supervisor and user. Computer executable logic for implementing the interactive overlay system resides on one or more of the system memory 606 and the memory devices 608, 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution, and can include multiple physical memory components linked to the processor via appropriate data connections.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system comprising:
a memory that stores computer executable components; and
a processor that executes at least the following computer executable components stored in the memory:
a monitoring component configured to receive at least one of biometric data or movement data for a user during performance of a fitness routine;
a parameter calculation component configured to determine whether the biometric data or the movement data is outside of a predefined range, and determine a desired behavior of the user in response to a determination that the biometric data or the motion data is outside of the predefined range;
an avatar rendering component configured to cause an avatar, presented to the user via a graphical user interface, to perform an action based on the desired behavior of the user, wherein the action includes speaking of a verbal command, by the avatar, that instructs the user regarding the desired behavior, and wherein the parameter calculation component is configured to determine the action based on a medical health history of the user.

2. The system of claim 1, wherein the biometric data comprises a heart rate of the user and the desired behavior comprises a modification to a manner of performance of an exercise by the user to a achieve a desired heart rate.

3. The system of claim 1, wherein the action includes speaking of the verbal command by the avatar using a specific tone of voice based on the desired behavior.

4. The system of claim 1, wherein the action includes a change in a facial expression of the avatar based on the desired behavior.

5. The system of claim 1, wherein the action includes speaking of the verbal command by the avatar using a specific volume based on the desired behavior.

6. The system of claim 1, further comprising a display component configured to render the graphical user interface on a device display of a device.

7. The system of claim 6, wherein the action further comprises movement of the avatar in a manner that reflects the desired behavior.

8. A method comprising:
receiving, by a device comprising a processor, at least one of biometric data or movement data for a user during performance of a physical activity;
determining, by the device, a modification to a manner of performance of the physical activity by the user based on comparison of the biometric data or movement data to predefined metrics associated with the physical activity, and based on a medical health history of the user; and
directing, by the device, included in a graphical user interface, to perform an action based on the modification, wherein the action includes speaking of a verbal command, by the avatar, that instructs the user regarding the modification.

9. The method of claim 8, further comprising:

presenting, by the device, the graphical user interface on a display of the device during performance of the physical activity.

10. The method of claim 8, wherein the biometric data comprises a heart rate of the user and the modification is configured to facilitate changing the heart rate of the user to a desired heart rate.

11. The method of claim 8, wherein the action includes speaking of the verbal command by the avatar using a specific tone of voice based on the modification.

12. The method of claim 8, wherein the action includes speaking of the verbal command by the avatar using a specific facial expression based on the modification.

13. The method of claim 8, wherein the action includes speaking of the verbal command by the avatar using a specific volume based on the modification.

14. A system comprising:

a memory that stores computer executable components; and a processor that executes at least the following computer executable components stored in the memory:

a monitoring component configured to receive at least one of biometric data or movement data for a user during performance of a fitness routine;

a parameter calculation component configured to determine whether the biometric data or the movement data is outside of a predefined range, and determine a desired behavior of the user in response to a determination that the biometric data or the motion data is outside of the predefined range;

an avatar rendering component configured to cause an avatar, presented to the user via a graphical user interface, to perform an action based on the desired behavior of the user, wherein the action includes speaking of a verbal command, by the avatar, that instructs the user regarding the desired behavior, including speaking of the verbal command using a specific tone of voice based on the desired behavior.

* * * * *